(12) United States Patent
Luxford et al.

(10) Patent No.: US 9,271,982 B2
(45) Date of Patent: Mar. 1, 2016

(54) ANIMAL FEED SUPPLEMENT COMPRISING RACTOPAMINE AND CAFFEINE

(71) Applicant: Rivalea (Australia) Pty Ltd, Corowa (AU)

(72) Inventors: Brian Gerard Luxford, Wangaratta (AU); Cherie Louise Collins, Corowa (AU)

(73) Assignee: Rivalea (Australia) Pty Ltd., Corowa (AU)

( * ) Notice: Subject to any disclaimer, the term of this patent is extended or adjusted under 35 U.S.C. 154(b) by 11 days.

(21) Appl. No.: 14/433,988

(22) PCT Filed: Oct. 8, 2013

(86) PCT No.: PCT/AU2013/001161
§ 371 (c)(1),
(2) Date: Apr. 7, 2015

(87) PCT Pub. No.: WO2014/056029
PCT Pub. Date: Apr. 17, 2014

(65) Prior Publication Data
US 2015/0265620 A1    Sep. 24, 2015

(30) Foreign Application Priority Data

Oct. 8, 2012    (AU) .................................. 2012904385

(51) Int. Cl.
A61K 31/522    (2006.01)
A61K 31/137    (2006.01)
A23K 1/18    (2006.01)
A23K 1/16    (2006.01)

(52) U.S. Cl.
CPC .............. *A61K 31/522* (2013.01); *A23K 1/1612* (2013.01); *A23K 1/1628* (2013.01); *A23K 1/1646* (2013.01); *A23K 1/184* (2013.01); *A61K 31/137* (2013.01)

(58) Field of Classification Search
None
See application file for complete search history.

(56) References Cited

U.S. PATENT DOCUMENTS

| | | |
|---|---|---|
| 3,852,451 A | 12/1974 | Cunningham |
| 4,690,951 A | 9/1987 | Anderson et al. |
| 5,422,352 A | 6/1995 | Astrup |

OTHER PUBLICATIONS

Collins et al., "Maintaining the response to ractopamine through intermittent feeding. 2H-102 Report prepared for the Co-operative Research Centre for an Internationally Competitive Pork Industry," Pork CRC, Jul. 2010, 1-13.
Li et al., "The Effect of Caffeine on Mammary Gland Development and Milk Yield in Primiparous Sows," J. Anim. Sci. 1995, 73:534-540.
Oksbjerg et al., "Separate and combined effects of ephedrine and caffeine on protein and lipid deposition in finishing pigs," Animal Science 1995, 60:299-305.
International Preliminary Report on Patentability, International application No. PCT/AU2013/001161, Mar. 14, 2014, 7 pages.

*Primary Examiner* — Yevegeny Valenrod
(74) *Attorney, Agent, or Firm* — Morgan, Lewis & Bockius LLP

(57) ABSTRACT

An animal feed supplement comprising a synergistic combination of ractopamine and caffeine and a method of increasing feed efficiency of a pig using the animal feed supplement is described.

23 Claims, 5 Drawing Sheets

ANIMAL FEED SUPPLEMENT COMPRISING RACTOPAMINE AND CAFFEINE

CROSS-REFERENCE TO RELATED APPLICATIONS

This application is the United States national stage application of International Patent Application No. PCT/AU2013/001161, filed Oct. 8, 2013, which claims priority to Australian Patent Application No. 2012904385, filed Oct. 8, 2012, the entire contents of each of which are specifically incorporated herein by reference.

TECHNICAL FIELD

The present invention relates generally to animal feed supplements and particularly to methods to improve feed efficiency in pigs.

BACKGROUND

Growth supplements, biologically active agents such as hormones and growth factors, and antibiotics have been used in animal diets to improve yields and carcass conditioning. As the demand for protein increases in the world, animal producers require improved feeds and feed supplements to assist in output of intensive livestock farming practices.

Ractopamine hydrochloride (RAC, Paylean™, Elanco Animal Health, Greenfield, Ind.)) is a beta adrenergic agonist ($\beta$-agonist) that is approved for use as an in feed ingredient for pigs. RAC is a widely used pig feed ingredient, approved for use in most major pork-producing countries, that directs nutrients to increase the amount of lean pork while maintaining meat quality. RAC has been widely demonstrated to improve feed efficiency and growth rates both in Australia (Dunshea et al. 1993 *Journal of Animal Science* 71: 2931-2941; Smits and Cadogan, 2003 *Recent Advances in Animal Nutrition in Australia,* Volume 14, Ed J. L. Corbett, Page 143-150) and overseas (Watkins et al. 1990 *Journal of Animal Science,* 68:3588-3595). RAC is a growth promoter but also keeps pigs leaner.

The present inventors have developed an improved animal feed supplement and methods to improve feed efficiency of animals.

DISCLOSURE OF INVENTION

In a first aspect there is provided an animal feed supplement comprising a synergistic combination of ractopamine and caffeine.

Preferably, the ractopamine is ractopamine hydrochloride.

Preferably, the supplement is for Use as a pig feed finishing diet.

The animal feed supplement can have a ratio of ractopamine to caffeine of from about 1:100 to 1:10.

The animal feed supplement can have a ratio of ractopamine to caffeine of about 1:100, 1:95, 1:90, 1:185, 1:80, 1:76, 1:70, 1:65, 1:60, 1:55, 1:50, 1:45, 1:40, 1:35, 1:30, 1:25, 1:20, 1:15, 1:10.

Preferably the ratio of ractopamine to caffeine is about 1:50 to 1:100. A ratio of about 1:70 was found to be particularly useful but it will be appreciated that other ratios would be suitable. Commercially ractopamine is registered for use in pigs up to 20 ppm and would be commonly used at rates between about 5 ppm and 15 ppm. In other countries, such as the United States of America, typically use ractopamine at about 5 ppm in animal feeding.

The animal feed supplement can be formulated as a free-flowing granular material that can be added to bulk feed to provide the desired amounts of ractopamine and caffeine in the feed for consumption by animals. For example, the supplement contains 20 grams of ractopamine hydrochloride (active ingredient) and 1400 grams of caffeine (active ingredient) per kilogram of product.

The animal feed supplement is preferably packaged in 10 kg laminated bags with moisture barrier within the plies.

The animal feed supplement can contain from about 1 to 100 g/kg ractopamine or about 1 to 50 g/kg ractopamine hydrochloride and from about 10 to 3000 g/kg caffeine, or about 50 to 2000 g/kg caffeine or about 50 to 950 g/kg caffeine for mixing with bulk complete animal feed to provide a desired final concentration of ractopamine and caffeine to the animal feed.

Preferably, the animal fee supplement contains at least about 10 g/kg ractopamine hydrochloride and at least about 500 g/kg caffeine. Preferably, the supplement contains at least about 1% (w/w) ractopamine and at least about 50% (w/w) caffeine, preferably about 70% (w/w) caffeine. The supplement is preferably added to bulk animal feed to obtain a final concentration of at least about 5 mg/kg ractopamine and at least about 0.5 g/kg caffeine.

The animal feed supplement is particularly useful in finishing pigs prior to slaughter and meat processing. The pigs are typically fed for at least 14 days and usually over a period of about 35+ days. Pigs typically are about 16 weeks of age and weigh in the order of 60 kg at the start time of feeding the supplement. It will be appreciated that pigs of other starting weights, lighter or heavier, can be used.

The present inventors have found that the feed supplement containing caffeine allows the maximum response of feeding ractopamine to be extended for an additional period of at least about 14 days.

In a second aspect, there is provided a method of increasing feed efficiency of a pig, the method comprising feeding to a pig over a period of time an animal feed containing animal feed supplement according to the first aspect of the present invention.

In a third aspect there is provided a method of increasing feed efficiency of a pig, the method comprising feeding to a pig over a period of time an animal feed supplemented with a synergistic combination of ractopamine and caffeine.

The ractopamine and caffeine may be provided to the animal feed in combination as a feed supplement or provided individually to bulk feed to obtain the desired amounts of ractopamine and caffeine in the feed.

Preferably, the animal feed is formulated as a finisher diet for pigs.

The animal feed after supplementation can have from about 1 mg/kg to 50 mg/kg (w/w) ractopamine and from about 0.02 g/kg to 5 g/kg (w/w) caffeine. Preferably, the animal feed after supplementation can have from about 5 mg/kg to 20 mg/kg (w/w) ractopamine and from about 0.1 g/kg to 1 g/kg (w/w) caffeine. Preferably, a final concentration of about 7.5 ppm ractopamine and about 0.5 KO caffeine is used in the bulk feed. A final concentration of about 5 ppm ractopamine and about 0.5 kg/t caffeine can also be used in the bulk feed.

Preferably, the animal feed contains at least about 7.5 mg/kg ractopamine and at least about 0.5 g/kg caffeine. It will be appreciated that other concentrations can be used, The present inventors have found that the ractopamine may be present in the animal feed at an amount of about 0.0375% (w/w) and the caffeine may be present in the animal feed at an amount of about 0.05% (w/w).

An animal feed supplement containing about 20 g/kg ractopamine hydrochloride and 1400 k/kg caffeine when included in complete feed to a final concentration of about 7.5 ppm combined with caffeine included in complete feed at 0.5 kg/t has been found to be particularly useful. l.

The pig can be fed over a period of at least 14 days and up to about 60 days. Preferably, the pig is fed over a period of at least 26 days to improve feed efficiency of the pig above that generally observed with RAC alone over the same period of time.

The animal feed to which the supplement is added is a typical pig finishing feed containing the essential dietary requirements for the pig. A typical finisher feed for growing pigs is formulated to meet these nutritional specifications using a range of energy and protein sources including but not limited to wheat, barley, sorghum, corn, soybean meal, lupins, canola meal, meat meal and bone meal. An example of a typical Australian finisher diet is displayed in Table 1.

A particularly useful animal feed to which the supplement is added is a pig finishing feed containing approximately 13.8 MJ digestible energy (DE)/kg, 14-15% crude protein, approximately 3% crude fat, approximately 3-4% crude fibre and a minimum available lysine:DE ratio of 0.48 g/MJ DE. It will be appreciated that that diet specifications may differ depending on age, weight, sex, and genotype of the animal as well as the dietary ingredients available locally to the producer.

The present inventors have found that the feed efficiency of pigs may be improved by about 1 to 5% using the feed supplement containing the synergistic combination of ractopamine and caffeine according to the present invention.

In a preferred form, the increase in feed efficiency is up to about 5% improvement above feeding ractopamine alone.

Feeding with the supplement is preferably for at least about 2 weeks. Preferably, pigs are fed for 21 to 36 days. The response may be observed for even longer periods of time and may be used in combination with feeding RAC alone for an initial 2-3 week period followed by the addition of the feed supplement containing both RAC and caffeine for a further period of at least 14 days.

The addition of caffeine to a ractopamine finisher diet can extend the benefits from ractopamine feeding beyond the usual 3 weeks. This outcome would be particularly beneficial for production of heavier carcass weights.

Feed efficiency is defined as the mass of food eaten/body mass gain over a specified period.

In a fourth aspect there is provided an improved pig feed containing essential dietary requirements and a synergistic combination of ractopamine and caffeine.

Preferably the improved pig feed is formulated to meet required nutritional specifications using a range of energy and protein sources including but not limited to wheat, barley, sorghum, corn, soybean meal, lupins, canola meal, meat meal and bone meal.

Preferably, the pig feed is formulated as a finisher diet for pigs. The improved pig feed can have from about 1 mg/kg to 50 mg/kg (w/w) ractopamine and from about 0.02 g/kg to 5 g/kg (w/w) caffeine. Preferably the improved pig feed can have from about 5 mg/kg to 20 mg/kg (w/w) ractopamine, and from about 0.1 g/kg to 1 g/kg (w/w) caffeine. A final concentration of about 7.5 ppm ractopamine and about 0.5 kg/t caffeine has been found to be particularly useful as a finishing diet for pigs.

A final concentration of about 5 ppm ractopamine and about 0.5 kg/t caffeine can also be used in the improved pig feed.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

In order that the present invention may be more clearly understood, preferred embodiments will be described with reference to the following drawings and examples.

MODE(S) FOR CARRYING OUT THE INVENTION

Figure 1:
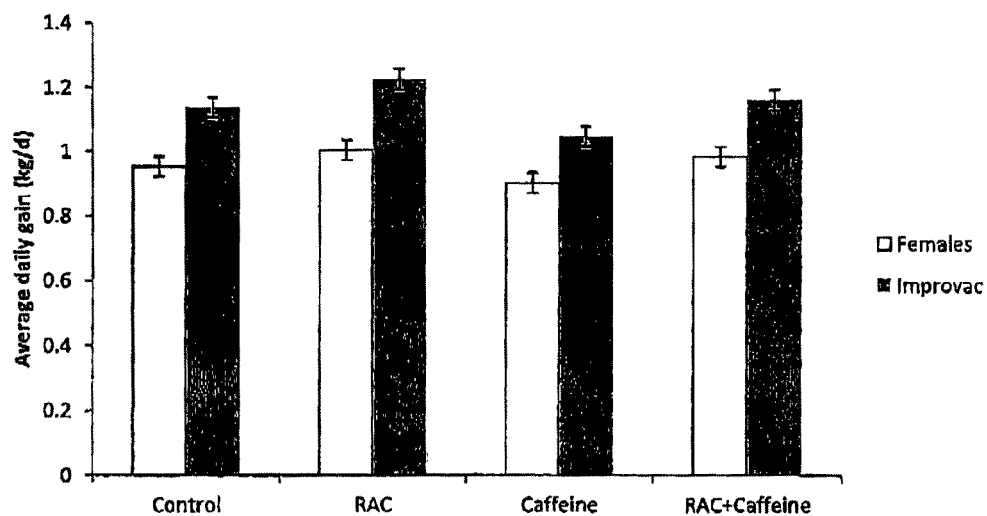
FIG. 1 shows results of influence of diet on rate of gain over an entire test period. Significance: Sex $P<0.001$, Diet $P<0.001$, Sex×diet $P=0.38$
Figure 2:
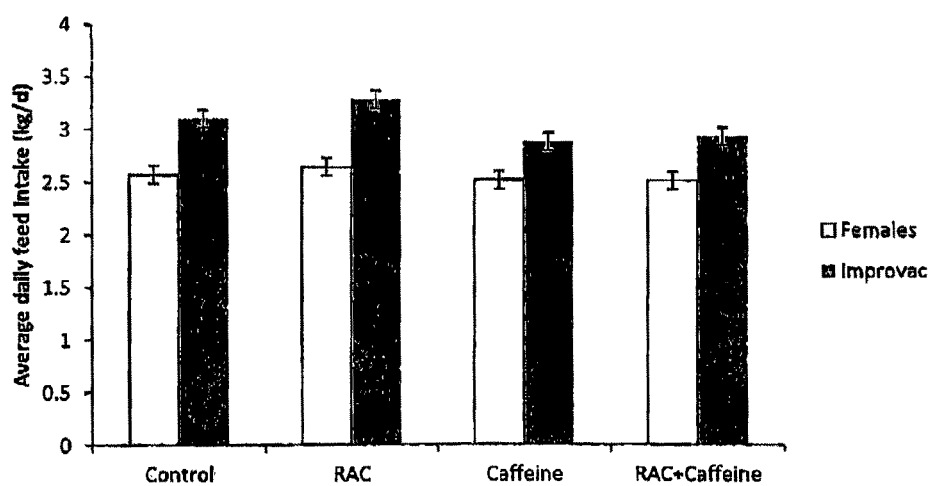
FIG. 2 shows results of influence of diet on average daily feed intake ver an entire test period. Significance: Sex P<0.001, Diet P<0.001, Sex×diet P=0.091
Figure 3:
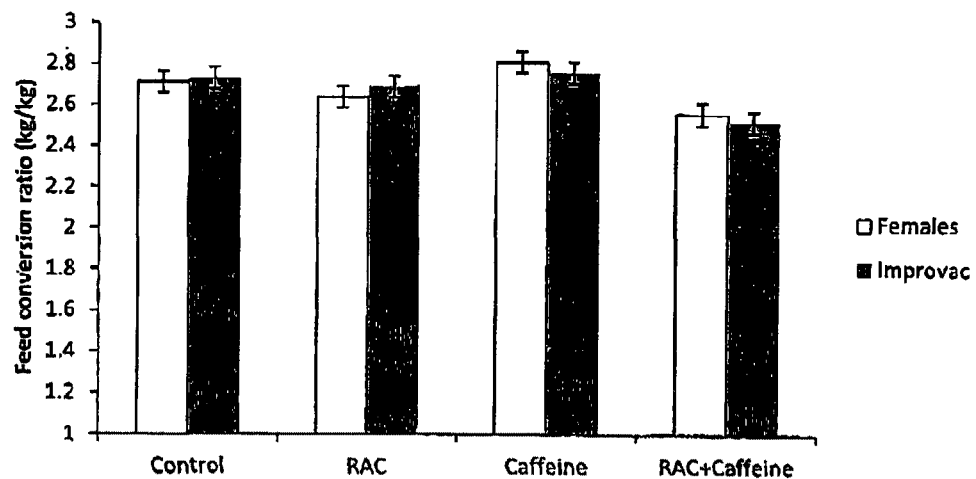
FIG. 3 shows results of influence of diet on feed efficiency over an entire test period. Significance: Sex P=0.82, Diet P<0.001, Sex×diet P=0.52.
Figure 4:
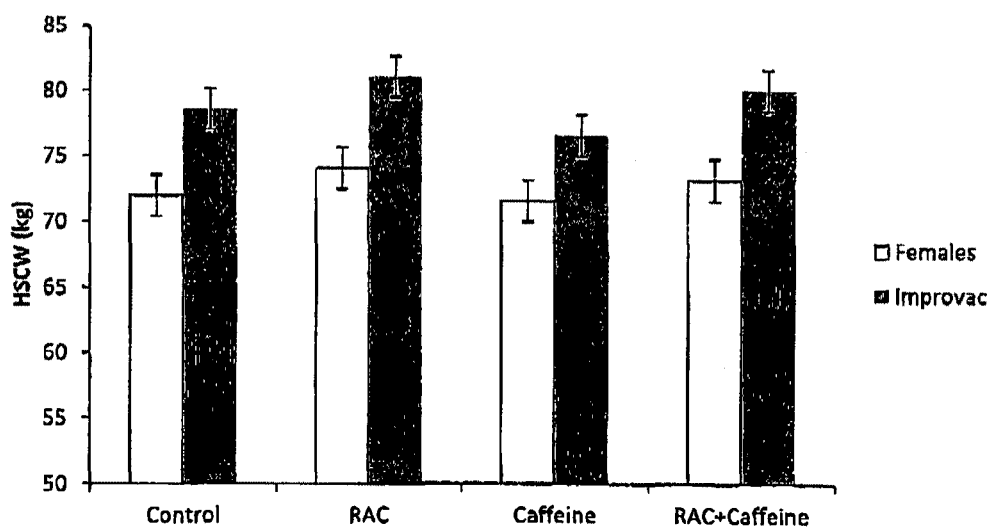
FIG. 4 shows results of influence of diet on carcass weight. Significance: Sex P<0.001, Diet P=0.014, Sex×diet P=0.90.
Figure 5:
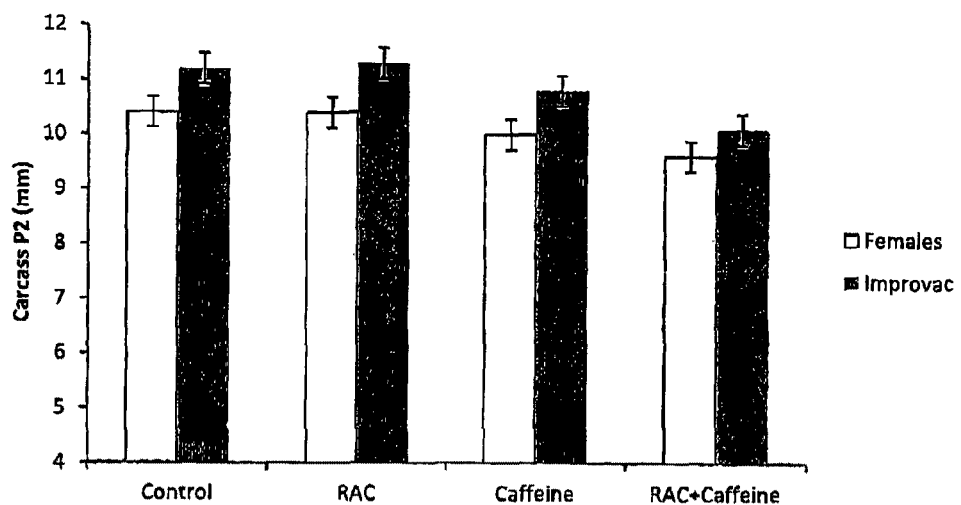
FIG. 5 shows results of influence of diet on carcass P2 (HSCW used as a covariate in the analysis). Significance: Sex P<0.001, Diet P<0.001, Sex×diet P=0.64.
Figure 6:
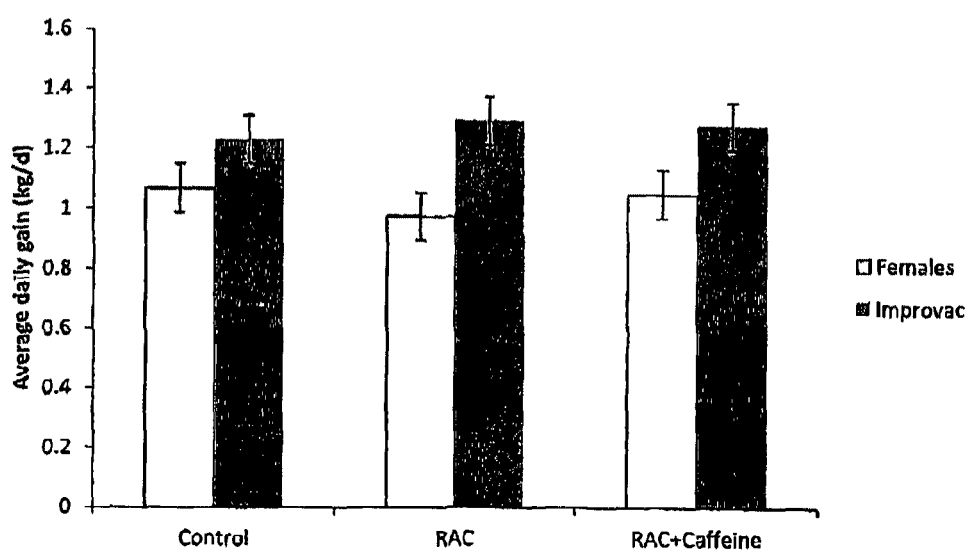
FIG. 6 shows results of influence of diet on rate of gain over an entire test period. Significance: Sex P<0.001, Diet P=0.88, Sex×diet P=0.38.
Figure 7:
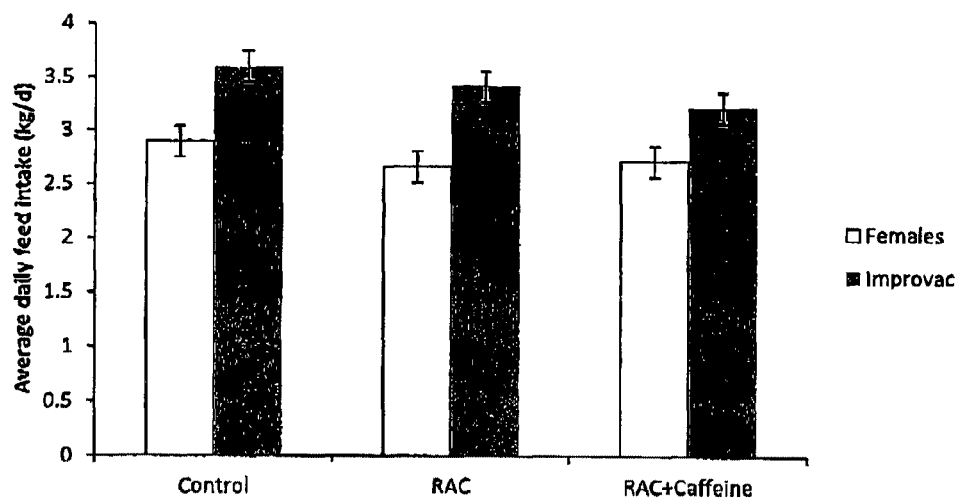
FIG. 7 shows results of influence of diet on average daily feed intake over an entire test period. Significance: Sex P<0.001, Diet P=0.020, Sex×diet P=0.45.
Figure 8:
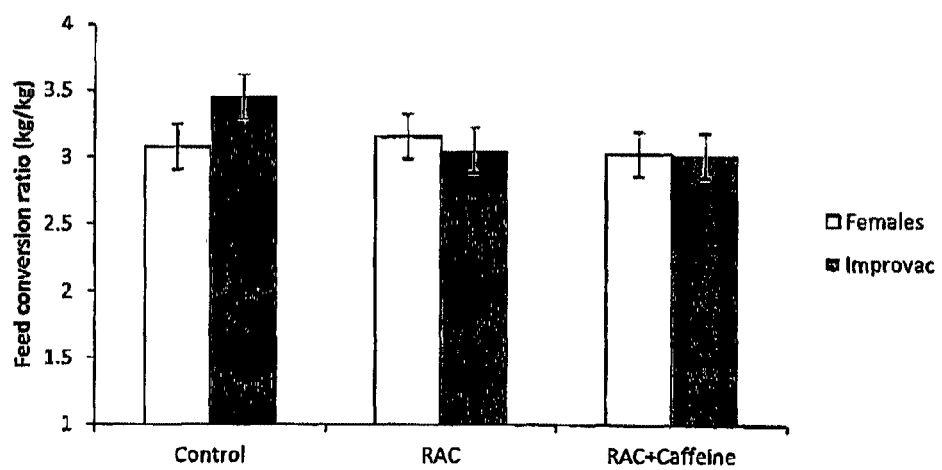
FIG. 8 shows results of Influence of diet on feed efficiency over an entire test period. Significance: Sex P=0.37, Diet P=0.12, Sex×diet P=0.106.
Figure 9:
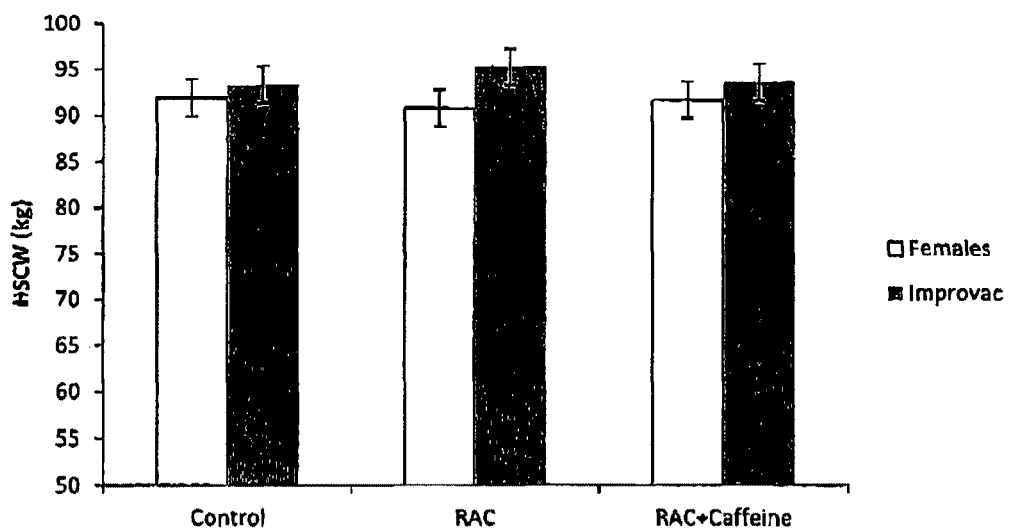
FIG. 9 shows results of influence of diet on carcass weight. Significance: Sex P=0.024, Diet P=0.95, Sex×diet P=0.49.
Figure 10:
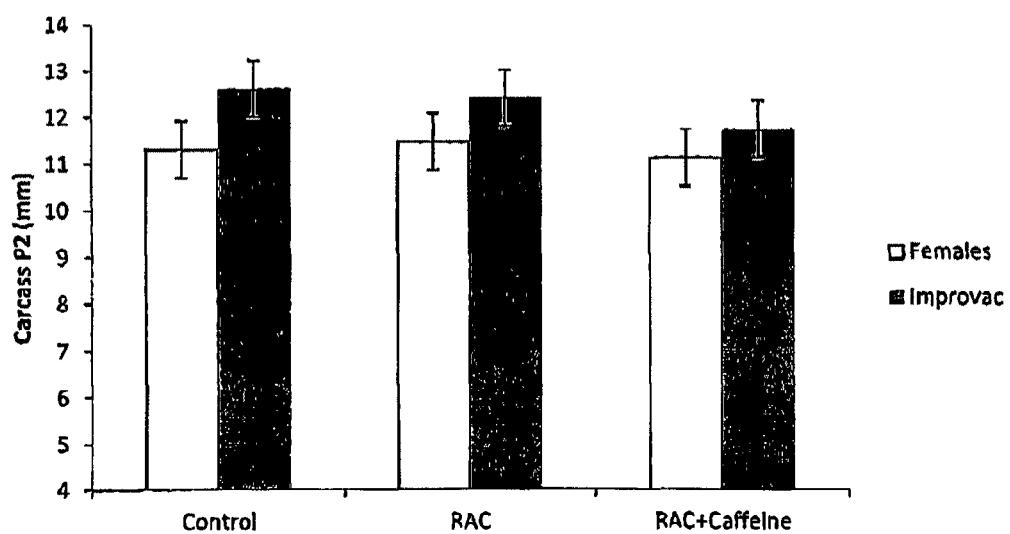
FIG. 10 shows results of influence of diet on carcass P2 (HSCW used as a covariate in the analysis). Significance: Sex P<=0.009, Diet P=0.39, Sex×diet P=0.71.

Ractopamine (RAC) is a beta adrenergic agonist (β-agonist) that is approved for use as an in feed ingredient for pigs. RAC has been widely demonstrated to improve feed efficiency and growth rates both in Australia (Dunshea at al 1993, Smits and Cadogan, 2003) and overseas (Schinckel et al 2001). Paylean™ is commonly included in finisher diets from Autumn through to Spring to improve growth rates and the efficiency of feed utilisation, however the use of Paylean™ during autumn has been questioned with overweight pigs a significant issue at this time of the year.

The management of weight and carcass P2 during Autumn is critical in markets that are paid on a grid of both parameters. The rate of fat deposition is at a maximum during the finisher period and is related to the amount of energy consumed by the pig. Excess energy intake above that required for protein deposition during this time is deposited as fat. As such, strategies to reduce feed intake from the excessive highs during autumn are often implemented. Caffeine is one ingredient that can be included in finisher diets to limit excessive feed intake. A study evaluating caffeine inclusion rates was conducted with the results confirming the intake restricting effects of caffeine inclusion. Feed intake was reduced from 2.62 kg/d to 2.45 and 2.33 kg/d with caffeine included in the diet at either 0.5 kg/t or 0.75 kg/t respectively. This restriction on feed intake was able to reduce growth rates by 95 and 163 g/d respectively. There has however been no evaluation of the effects of caffeine inclusion when the finisher diet also contains Paylean™. As such, the aim of this study was to determine the effects of caffeine inclusion when Paylean™ is also present in the finisher diet.

Ractopamine

Ractopamine (RAC) is sold by Elanco Animal Health (Greenfield, Ind. USA) under the brand Paylean™ as a free-flowing granular material, manufactured to provide 20 grams of ractopamine hydrochloride (active ingredient) per kilogram of product. Paylean™ is packaged in 10 kg laminated bags with moisture barrier within the plies. Paylean™ is manufactured to meet three-year expiry dating.

The manufacture offers the following information on its Paylean™ product.

Paylean™ is marketed for increased carcass leanness, increased dressing percent, improved rate of weight gain and improved feed efficiency by feeding pigs at 10 mg/kg (0.001%) of the complete feed. Thoroughly mix 500 grams of Paylean™ Premix in 1000 kg of complete swine feed (90% dry matter basis) to provide 10 g ractopamine HCl per tonne of feed. To ensure adequate mixing, an intermediate blending step should be performed prior to manufacturing a complete feed.

Paylean™ is also marketed for improved rate of weight gain and feed efficiency by feeding 5 mg/kg-10 mg/kg (0.0005%-0.001%) of the complete feed. Thoroughly mix 250 grams of Paylean™ Premix in 1000 kg of complete swine feed (90% dry matter basis) to provide 5 g ractopamine HCl per tonne of feed. To ensure adequate mixing, an intermediate blending step should be performed prior to manufacturing a complete feed.

Directions are to feed continuously as the sole ratio to finishing swine intended for slaughter for no longer than 6 weeks. To obtain the performance benefits of ractopamine HCl, diets should contain a minimum of 16% crude protein or its equivalent obtained by amino acid (0.85%-0.95% lysine) fortification. Dietary specifications should be determined in consultation with a recognized nutritional advisor in order to optimize Paylean™ effects on performance, carcass parameters and pork quality.

Caffeine

Caffeine was obtained from CSPC Innovation Pharmaceutical Co Ltd—a Chinese off-patent manufacturer. Caffeine is readily available in bulk from fine chemical suppliers. Caffeine can be added to the complete animal feed at a concentration of from about 0.02 g/kg to 5 g/kg (w/w) caffeine. Preferably, the animal feed after supplementation can have from about 0.1 g/kg to 1 g/kg (w/w) caffeine. Preferably, a final concentration of about 0.5 kg/t caffeine is used in the bulk feed.

Animal Feed Supplement

An animal feed supplement containing ractopamine and caffeine can be prepared by adding caffeine to a bulk pack of Paylean™ to provide the desired concentrated amounts of ractopamine and caffeine. The feed supplement can then be added to bulk animal feed to provide the desired amounts of ractopamine and caffeine to be consumed by the animal.

In one embodiment, the animal feed supplement can contain from about 1 to 50 g/kg ractopamine hydrochloride and from about 50 to 950 g/kg caffeine for mixing with bulk complete animal feed to provide a desired final concentration of ractopamine and caffeine to the animal feed.

Ractopamine and caffeine can be mixed in any suitable carrier materiel, such as milled grain or other edible material and pelleted by standard techniques to give a concentrated supplement for adding to animal feed to give a final desired feeding quantity of ractopamine and caffeine.

Animal Feed

The animal feed is a typical pig finishing feed containing the essential dietary requirements for the pig. A typical finisher feed for growing pigs is formulated to meet these nutritional specifications using a range of energy and protein sources including but not limited to wheat, barley, sorghum, corn, soybean meal, lupins, canola meal, meat meal and bone meal. An example of a typical Australian finisher diet is displayed in Table 1.

A particularly useful animal feed to which the supplement is added is a pig finishing feed containing approximately 13.8 MJ digestible energy (DE)/kg, 14-15% crude protein, approximately 3% crude fat, approximately 3-4% crude fibre and a minimum available lysine:DE ratio of 0.48 g/MJ. It will be appreciated that that diet specifications may differ depending on age, weight, sex, and genotype of the animal as well as the dietary ingredients available locally to the producer.

The desired amounts of ractopamine and caffeine can be added separately to the bulk feed or can be provided by adding an animal feed supplement containing ractopamine and caffeine.

The supplemented animal feed can have from about 1 mg/kg to 50 mg/kg (w/w) ractopamine and from about 0.02 g/kg to 5 g/kg (w/w) caffeine. The animal feed after supplementation can have from about 5 mg/kg to 20 mg/kg (w/w) ractopamine and from about 0.1 g/kg to 1 g/kg (w/w) caffeine. A final concentration of about 7.5 ppm ractopamine and about 0.5 kg/t caffeine has been found to be particularly useful for pigs in a finishing diet.

Study 1—Effects of Ractopamine (Paylean™) and Caffeine on Growth and Carcass Characteristics when Used in Combination During Autumn Materials and Methods Animals and Treatments A total of 1212 pigs (female and Improvac™ vaccinated males, Large White×Landrace, PrimeGro™ Genetics) were identified at 16 weeks of age in commercial grower/finisher accommodation (pens of 10-14 pigs of the same sex). Pigs were selected to start on trial over three days during week 20 of the test year. Prior to the start of the trial, all pigs were offered a commercial grower diet (no Paylean™) and had been in their allocated pens from 13 weeks of age. At 16 weeks of age, pen weights were recorded (average pig weight 61.2 kg±0.44 kg) and pens randomly allocated within sex to one of 4 dietary treatments (A: control, no RAC or Caffeine; B: 7.5 ppm RAC; C: 0.5 kg/t caffeine; D; 7.5 ppm RAC and 0.5 kg/t caffeine). All diets were fed for the entire 35 day test period. The dietary compositions of the four experimental diets are displayed in Table 1. All diets were formulated to contain 0.62 g available lysine/MJ DE and 13.8 MJ DE/kg. Diets were pelleted and fed ad libitum from 16 weeks of age through to slaughter at 21 weeks of age. All animals had ad libitum access to water via nipple drinkers for the entire experimental period.

Improvac™ vaccine (Pfizer Animal Health) is comprised of a synthetic, incomplete analogue of natural gonadotrophin-releasing factor (GnRF) which is conjugated to a carrier protein. Improvac™ is routinely used on male pigs to reduce the presence of the two major sources of boar taint (androstenone and skatole) without resorting to physical castration.

Management and Measures

Growth Performance

All male pigs received a priming vaccination of Improvac™ at 13 weeks of age and the second vaccination at 16 weeks of age (during the first week of the experimental period). Pen weights were recorded at the beginning of the experimental period (day 0, 1-7 weeks of age) and again at day 14 and day 35 (prior to slaughter). Pen feed intakes were also recorded over these time periods as measured by feed disappearance and feed conversion efficiency subsequently calculated. All deaths and removals were recorded and taken into account when calculating feed intake and feed efficiency by the adjustment of the number of days that pigs were on trial.

Statistical Analyses

Data were subjected to an analysis of variance (ANOVA) with the main effects being dietary treatment and sex. Replicate (start date within week) was included in the analyses to account for the blocking factor. The experimental unit for all analyses was the pen of pigs. All analyses were performed using Genstat 8th Edition (Payne R W, Harding S A, Genstat Committee 2005 Genstat release 8 reference manual, USN International: Oxford UK)

TABLE 1

Ingredient composition and analysed nutrient profile of each of the experimental finisher diets, % of diet (as fed basis).

|  | Control | RAC | Caffeine | RAC + caffeine |
|---|---|---|---|---|
| Wheat | 72.8 | 72.8 | 72.8 | 72.8 |
| Lupin Kernels 33% | 7.0 | 7.0 | 7.0 | 7.0 |
| Millmix | 11.3 | 11.3 | 11.3 | 11.3 |
| Canola Meal 36% | 1.7 | 1.7 | 1.7 | 1.7 |
| Meat meal | 3.0 | 3.0 | 3.0 | 3.0 |
| Water | 1.0 | 1.0 | 1.0 | 1.0 |
| Natuphos 5000 | 0.01 | 0.01 | 0.01 | 0.01 |
| Tallow-Mixer | 0.80 | 0.80 | 0.80 | 0.80 |
| Limestone | 1.40 | 1.40 | 1.40 | 1.40 |
| DL-Methionine | 0.05 | 0.05 | 0.05 | 0.05 |
| Copper Proteinate | 0.075 | 0.075 | 0.075 | 0.075 |

TABLE 1-continued

Ingredient composition and analysed nutrient profile of each of the experimental finisher diets, % of diet (as fed basis).

| | Control | RAC | Caffeine | RAC + caffeine |
|---|---|---|---|---|
| Paylean ™ Premix | 0.0 | 0.0375 | 0.0 | 0.0375 |
| Lysine Micro | 0.38 | 0.38 | 0.38 | 0.38 |
| Threonine Micro | 0.14 | 0.14 | 0.14 | 0.14 |
| Vitamin & minerals | 0.09 | 0.09 | 0.09 | 0.09 |
| Salt Bin Micro | 0.2 | 0.2 | 0.2 | 0.2 |
| Clostat Dry Micro | 0.1 | 0.1 | 0.1 | 0.1 |
| Salinodox 120 Micro | 0.05 | 0.05 | 0.05 | 0.05 |
| Caffeine | 0.0 | 0.0 | 0.05 | 0.05 |
| Estimated nutrient composition, %* | | | | |
| DE, MJ/kg | 13.76 | 13.76 | 13.76 | 13.75 |
| Crude protein | 15.49 | 15.48 | 15.48 | 15.48 |
| Crude fat | 2.78 | 2.78 | 2.78 | 2.78 |
| Crude fibre | 3.30 | 3.30 | 3.30 | 3.30 |
| Total Lysine | 0.86 | 0.85 | 0.85 | 0.86 |
| Available lysine:DE ratio g/MJ DE | 0.54 | 0.54 | 0.54 | 0.54 |

*Estimated from Rivalea Australia Pty Ltd composition data

Results

There were no effects of the dietary treatments on animal welfare during the study. The deaths and removals from each of the dietary treatments are displayed in Table 2. Deaths were similar across the four dietary treatment groups—control (1/305, 0.33%), RAC (2/298, 0.67%), Caffeine (2/307, 0.65%), RAC+caffeine (4/302 1.32%), $\chi 2=2.15$, $P=0.54$. There was also no significant effect of diet on removals during the test period ($\chi 2=2.80$, $P=0.48$).

TABLE 2

Impact of diet on deaths and removals during the entire test period

| | 0-14 days | | | | 14-35 days | | | | |
|---|---|---|---|---|---|---|---|---|---|
| | Control | RAC | Caff | RAC + Caff | Control | RAC | Caff | RAC + Caff | Total |
| Deaths | | | | | | | | | |
| Ileitis | | | | | 1 | 1 | 1 | 3 | 6 |
| Hernia | | | | | | 1 | | | 1 |
| SD | | | | | | | 1 | 1 | 2 |
| Off trial | | | | | | | | | |
| APP | 1 | | | | | | | 1 | 2 |
| Lame | 2 | 1 | | 1 | | 1 | 1 | | 6 |
| Unthrifty | 1 | | | 1 | | | | 2 | 4 |
| Prolapse | 1 | | | | | | | | 1 |
| Wound | | 1 | | | | | | | 1 |
| Meningitis | | 1 | | | | | 1 | | 2 |
| Missing | | | | | | 1 | | 1 | 2 |
| TOTAL | 5 | 3 | 0 | 2 | 2 | 3 | 4 | 8 | |

The impact of RAC and/or caffeine inclusion during autumn on finisher growth performance and feed consumption is displayed in Table 3. During the initial 14 day feeding period, pigs offered the caffeine diet consumed less feed and gained weight more slowly than the control or RAC treatment groups. Feed efficiency was poorer with the addition of caffeine alone compared to the control diet during this time. RAC inclusion alone during the initial 14 day period resulted in an increase in feed intake and an improvement in rate of gain without any significant effects on feed efficiency. The addition of caffeine to the RAC diet lessened the growth promoting effect of RAC while maintaining a similar feed efficiency to the control diet.

During the subsequent period from day 14 to 35, rate of gain was greatest in the pigs offered the combined diet of RAC+caffeine. Interestingly, this treatment group also utilised feed more efficiently than the other treatment groups during this time (approximate 10% improvement in feed efficiency compared to the pigs offered RAC alone). Over the entire test period, the inclusion of caffeine alone significantly reduced feed intake and rate of gain, with a numerical increase in feed conversion ratio. RAC fed alone for the entire test period improved daily rate of gain without any significant changes in feed efficiency. The combination of RAC+caffeine resulted in numerical reductions in feed intake and a slight increase in growth rate compared to the control pigs, however feed efficiency was substantially improved.

The responses of both sexes to the dietary treatments are shown in FIGS. 1 through to 5. The inclusion of caffeine alone reduced carcass weight compared to either of the RAC treatment groups, while pigs offered the RAC+caffeine treatment displayed carcass weights statistically similar to the controls. Including weight as a covariate in the analysis, P2 back fat depth was significantly reduced with the combination treatment compared to all of the other treatment groups. Of importance to the domestic Australian market, the percentage of pigs with a P2 backfat depth greater than 12 mm was markedly reduced (either with or without carcass weight as a covariant Implications The results from this investigation supports that there may be synergistic effects from the use of RAC in combination with caffeine. In particular, the addition of caffeine to a RAC finisher diet extended the benefits from RAC feeding beyond the usual 3 weeks (improved growth, feed efficiency and reduced carcass P2). It is hypothesised that the magnitude of this benefit would be greater the heavier the carcass weight. The substantial reduction in the percentage of pigs with a P2 backfat depth greater than 12 mm in the RAC+caffeine treatment group offers a new technical approach to ensuring the maximum number of pigs reach the premium carcass grade specifications.

TABLE 3

Influence of dietary RAC and/or caffeine addition on the feed intake and growth performance of finisher gilts and Improvac ™ males during autumn

| | Sex | | SED | Feeding Strategy | | | | SED | Significance | | |
|---|---|---|---|---|---|---|---|---|---|---|---|
| | Female | Improvac | Sex | Control | RAC 7.5 ppm | Caffeine 0.5 kg/t | RAC + caffeine | Diet | Sex | Diet | Sex × diet |
| Live weight | | | | | | | | | | | |
| Day 0 | 58.9 | 63.4 | 0.75 | 61.2 | 61.2 | 61.3 | 61.2 | 1.06 | <0.001 | 1.00 | 0.99 |
| Day 14 | 72.7 | 78.9 | 0.86 | 76.3 | 77.6 | 74.2 | 75.2 | 1.22 | <0.001 | 0.045 | 0.88 |
| Day 35 | 92.5 | 103.4 | 1.07 | 97.7 | 100.1 | 95.3 | 98.7 | 1.52 | <0.001 | 0.018 | 0.88 |
| 0-14 days | | | | | | | | | | | |
| ADG (g/d) | 0.986 | 1.104 | 0.017 | 1.078 | 1.170 | 0.927 | 1.003 | 0.024 | <0.001 | <0.001 | 0.013 |
| ADFI (kg/d) | 2.44 | 2.62 | 0.036 | 2.56 | 2.72 | 2.44 | 2.40 | 0.051 | <0.001 | <0.001 | 0.23 |
| FCR (kg/kg) | 2.50 | 2.39 | 0.031 | 2.39 | 2.34 | 2.64 | 2.41 | 0.044 | 0.002 | <0.001 | 0.60 |
| 14-35 days | | | | | | | | | | | |
| ADG (g/d) | 0.941 | 1.167 | 0023 | 1.019 | 1.073 | 1.005 | 1.118 | 0.032 | <0.001 | 0.002 | 0.93 |
| ADFI (kg/d) | 2.64 | 3.34 | 0.050 | 3.02 | 3.13 | 2.88 | 2.94 | 0.072 | <0.001 | 0.005 | 0.091 |
| FCR (kg/kg) | 2.83 | 2.87 | 0.046 | 2.97 | 2.92 | 2.89 | 2.63 | 0.064 | 0.35 | <0.001 | 0.15 |
| 0-35 days | | | | | | | | | | | |
| ADG (g/d) | 0.959 | 1.142 | 0.015 | 1.043 | 1.112 | 0.974 | 1.072 | 0.022 | <0.001 | <0.001 | 0.38 |
| ADFI (kg/d) | 2.56 | 3.04 | 0.042 | 2.84 | 2.96 | 2.70 | 2.72 | 0.059 | <0.001 | <0.001 | 0.091 |
| FCR (kg/kg) | 2.68 | 2.67 | 0.026 | 2.72 | 2.67 | 2.78 | 2.54 | 0.037 | 0.82 | <0.001 | 0.52 |
| Carcass characteristics | | | | | | | | | | | |
| Carcass weight | 72.7 | 79.1 | 0.79 | 75.3 | 77.6 | 74.1 | 76.6 | 1.12 | <0.001 | 0.014 | 0.80 |
| Carcass P2 (mm)~~ | 10.1 | 10.9 | 0.17 | 10.8 | 10.9 | 10.4 | 9.9 | 0.19 | <0.001 | <0.001 | 0.64 |
| % pigs P2 >12 mm | 10.8 | 33.4 | 2.64 | 24.8 | 29.0 | 19.5 | 15.0 | 3.73 | <0.001 | 0.002 | 0.82 |
| % pigs P2 >12 mm~~ | 15.7 | 28.5 | 3.11 | 25.8 | 26.4 | 22.3 | 13.9 | 3.40 | <0.001 | <0.001 | 0.72 |
| Dressing % | 78.7 | 76.5 | 0.26 | 77.2 | 77.6 | 77.9 | 77.7 | 0.36 | <0.001 | 0.27 | 0.36 |

~~Carcass weight included as a covariate in the analysis

Study 2—Assessment of the RAC+Caffeine Strategy on Heavier Weight Finishers

The Australian market for heavy pigs is growing with the addition of large international wholesalers to the supermarket mix. The weight of carcasses supplied to other supermarkets has also risen slowly over the last 10 years. Increasing carcass weight has numerous efficiency improvements with the cost per kg of carcass weight produced reducing with the increased weight. In other major pig producing countries such as the United States of America, slaughter weight is much heavier than the current domestic Australian market.

The impact of the ractopamine (RAC)+caffeine feeding strategy in finisher pigs has not been assessed at these heavier weights. As such, the aim of this study was to assess the growth performance and feed efficiency of female and immunocastrated male pigs when offered a standard finisher diet from 22 to 26 weeks of age, or when this diet is supplemented with RAC or the combination treatment of RAC+caffeine to Improve growth rate, feed efficiency and carcass composition.

Materials and Methods

Animals and Treatments

A total of 168 pigs (female and immunocastrated males, Large White×Landrace, PrimeGro™ Genetics) were identified at 21 weeks of age and transferred into the research facility. Pigs were selected over a two week period. Pigs were weighed upon entry to the facility and allocated within sex to pens of 2 pigs per pen of similar body weight. At 22 weeks of age pigs were individually weighed and allocated on a pen basis to one of three treatments: A: Control; B: RAC 7.5 ppm, C: RAC 7.6 ppm+caffeine 0.5 kg/t. The dietary compositions of the three experimental diets are displayed in the Table 4 In this case the diets were formulated to mimic commercial production with the two RAC diets formulated to a higher lysine specification to enable the lean tissue deposition response to be observed. The interpretation of results is then a direct measure of the impact of commercial diets without RAC and commercial diets that do contain RAC. Diets were pelleted and fed ad libitum from 22 weeks of age through to slaughter at 26 weeks of age. All animals had ad libitum access to water via nipple drinkers for the entire experimental period.

TABLE 4

Ingredient composition and analysed nutrient profile of each of the experimental finisher diets, % of diet (as fed basis).

| | Control | RAC | RAC + Caffeine |
|---|---|---|---|
| Wheat | 85.7 | 82.47 | 82.47 |
| Millmix | 3.3 | 4.4 | 4.4 |
| Hull mix | 2.7 | | |
| Canola Meal 35% | 2.2 | 7.0 | 7.0 |
| Meat meal | 1.7 | 1.7 | 1.7 |
| Water | 1.0 | 1.0 | 1.0 |
| Natuphos 5000 | 0.01 | 0.01 | 0.01 |
| Tallow-Mixer | 0.70 | 0.70 | 0.70 |
| Limestone | 1.70 | 1.70 | 1.70 |
| DL-Methionine | 0.02 | 0.03 | 0.03 |
| Copper Proteinate | 0.08 | 0.075 | 0.075 |

TABLE 4-continued

Ingredient composition and analysed nutrient profile of each of the experimental finisher diets, % of diet (as fed basis).

| | Control | RAC | RAC + Caffeine |
|---|---|---|---|
| Paylean Premix | | 0.0375 | 0.0375 |
| Caffeine | — | — | 0.05 |
| Lysine Micro | 0.41 | 0.46 | 0.46 |
| Threonine Micro | 0.14 | 0.16 | 0.16 |
| Fysal SP Dry | | | |
| Vitamin and Minerals | 0.09 | 0.09 | 0.09 |
| Salt Bin Micro | 0.20 | 0.20 | 0.20 |
| Salinodox 120 Micro | 0.05 | 0.05 | 0.05 |
| Clostat | 0.05 | 0.05 | 0.05 |
| Estimated nutrient composition, %* | | | |
| DE, MJ/kg | 13.78 | 13.78 | 13.78 |
| Crude protein | 13.01 | 14.27 | 14.27 |
| Crude fat | 2.15 | 2.23 | 2.23 |
| Crude fibre | 3.81 | 2.45 | 3.45 |
| Available lysine:DE ratio g/MJ DE | 0.48 | 0.54 | 0.54 |

*Estimated from Rivalea Australia Pty Ltd composition data

Management and Measures

Growth Performance

The priming Improvac™ vaccinations were administered to the male pigs at 13 weeks of age, the secondary vaccination at 17 weeks of age, and a third vaccination at 21 weeks of age upon entry to the facility. Individual weights were recorded at entry, at the beginning of the experimental period (day 0, 22 weeks of age), day 14 and day 28 of the test period. Pen feed intakes were also recorded over these time periods as measured by feed disappearance and feed conversion efficiency subsequently calculated. All deaths and removals were recorded and taken into account when calculating feed intake and feed efficiency by the adjustment of the number of days that pigs were on trial. Pigs were slaughtered in a commercial abattoir at the conclusion of the test period. A subset of carcasses (n=12 per treatment) were randomly selected at the abattoir and followed through the boning room for meat yield assessment.

Statistical Analyses

Data were subjected to an analysis of variance (ANOVA) with the main effects being dietary treatment and sex. Replicate (start date within week) was included in, the analyses to account for the blocking factor. The experimental unit for all analyses was the pen of pigs. All analyses were performed using Genstat $8^{th}$ Edition (Payne et al. 2005).

Results

There were no negative effects of the dietary treatments on animal welfare during the study. There were no deaths during the test period, and only one animal removed from the study due to a leg injury.

The impact of dietary RAC and RAC+caffeine on growth performance, feed efficiency and carcass composition is displayed in Table 5. During the initial 14 day period, feed Intake was reduced in the pigs offered the RAC+caffeine strategy, while there was a slight reduction in growth rate (not significant). During the subsequent period (14-28 days), feed intake remained lower when pigs were offered the RAC+caffeine strategy while growth performance remained unaffected. The moderate improvement in feed efficiency during this time in the pigs offered RAC+caffeine compared to the RAC only diet was not statistically significant (2.4% improvement). Over the entire test period, feed intake was significantly reduced when the RAC or RAC+caffeine diets were offered, while there was a tendency for feed efficiency to be improved (P=0.12) with the RAC+caffeine diet. There was no significant impact of the dietary treatments on carcass weight, loin depth or dressing percentage. Despite this, there was a biologically significant reduction in P2 with the use of the RAC+caffeine strategy (average reduction of 0.5 mm). Both sexes responded similarly to the dietary treatments, with the outline of the Influence of sex on each of the performance parameters displayed in FIGS. 6 to 10.

The influence of dietary treatment on meat yield in the subset of carcasses followed through to the boning room is displayed in Table 6. Carcass weight was slightly higher than the larger population but did not differ between treatment groups. Carcass P2 was markedly lower (not significant) in the pigs offered the RAC+caffeine treatment in this subset of animals, while there was a strong trend for increased loin depth (P=0.078). The number of animals per treatment was insufficient to pick up any statistical differences in meat yield due to dietary treatment, however the numerical trends were interesting nonetheless. The percentage yield of the tenderloin was 4.6% greater in the pigs offered the RAC+caffeine treatment compared to RAC alone, while total fat from the middle was reduced by 16.4%.

TABLE 5

Influence of dietary RAC and/or caffeine addition on the feed intake and growth performance of finisher gilts and Improvac ™ males

| | Sex | | SED | Feeding Strategy | | | SED | Significance | | |
|---|---|---|---|---|---|---|---|---|---|---|
| | Female | Improvac | Sex | Control | RAC 7.5 ppm | RAC + caffeine | Diet | Sex | Diet | Sex × diet |
| Live weight | | | | | | | | | | |
| Day 0 | 91.8 | 92.7 | 0.93 | 92.3 | 92.1 | 92.3 | 1.14 | 0.34 | 0.97 | 0.97 |
| Day 14 | 104.4 | 107.9 | 1.08 | 106.5 | 106.0 | 105.9 | 1.32 | 0.002 | 0.88 | 0.71 |
| Day 28 | 117.2 | 123.5 | 1.63 | 120.9 | 120.1 | 120.1 | 2.00 | <0.001 | 0.91 | 0.45 |
| 0-14 days | | | | | | | | | | |
| ADG (kg/d) | 0.897 | 1.086 | 0.045 | 1.012 | 0.995 | 0.967 | 0.070 | 0.002 | 0.82 | 0.69 |
| ADFI (kg/d) | 2.65 | 3.23 | 0.085 | 3.08 | 2.92 | 2.82 | 0.104 | <0.001 | 0.045 | 0.36 |
| FCR (kg/kg) | 3.19 | 2.98 | 0.137 | 3.22 | 2.98 | 3.05 | 0.168 | 0.14 | 0.35 | 0.36 |
| 14-28 days | | | | | | | | | | |
| ADG (kg/d) | 0.919 | 1.115 | 0.066 | 1.026 | 1.008 | 1.016 | 0.081 | 0.004 | 0.98 | 0.21 |
| ADFI (kg/d) | 2.87 | 3.59 | 0.107 | 3.41 | 3.15 | 3.12 | 0.131 | <0.001 | 0.053 | 0.19 |
| FCR (kg/kg) | 3.29 | 3.31 | 0.172 | 3.41 | 3.28 | 3.20 | 0.211 | 0.90 | 0.62 | 0.64 |
| 0-28 days | | | | | | | | | | |
| ADG (kg/d) | 0.908 | 1.100 | 0.044 | 1.019 | 1.002 | 0.992 | 0.052 | <0.001 | 0.88 | 0.32 |
| ADFI (kg/d) | 2.76 | 3.41 | 0.083 | 3.25 | 3.04 | 2.97 | 0.102 | <0.001 | 0.020 | 0.45 |
| FCR (kg/kg) | 3.09 | 3.18 | 0.097 | 3.27 | 3.11 | 3.02 | 0.119 | 0.37 | 0.12 | 0.11 |
| Carcass characteristics | | | | | | | | | | |
| Carcass weight (kg) | 91.4 | 94.0 | 1.14 | 92.5 | 92.9 | 92.6 | 1.40 | 0.024 | 0.95 | 0.49 |
| Carcass P2 (mm) | 11.0 | 12.5 | 0.41 | 11.9 | 12.0 | 11.4 | 0.51 | <0.001 | 0.47 | 0.69 |
| Carcass P2 (mm)^^ | 11.3 | 12.3 | 0.36 | 12.0 | 11.9 | 11.4 | 0.43 | 0.009 | 0.39 | 0.71 |
| Loin depth (mm)^^ | 58.9 | 58.0 | 0.28 | 58.3 | 58.3 | 58.8 | 0.33 | <0.001 | 0.28 | 0.59 |
| Dressing % | 77.8 | 76.2 | 0.32 | 76.6 | 77.1 | 77.2 | 0.39 | <0.001 | 0.35 | 0.85 |

^^Carcass weight included as a covariate in the analysis

TABLE 6

Influence of dietary RAC and/or caffeine addition on carcass yield from a subset of carcasses (n = 12 per treatment)

| | Sex | | SED | Feeding Strategy | | | SED | Significance | | |
|---|---|---|---|---|---|---|---|---|---|---|
| | Female | Improvac | Sex | Control | RAC 7.5 ppm | RAC + caffeine | Diet | Sex | Diet | Sex × diet |
| HSCW (kg) | 92.6 | 94.2 | 1.05 | 93.1 | 93.4 | 93.6 | 1.28-1.31 | 0.14 | 0.91 | 0.99 |
| Carcass P2^^ (mm) | 12.1 | 11.7 | 0.77 | 12.6 | 12.2 | 10.9 | 0.90-0.92 | 0.66 | 0.19 | 0.86 |

TABLE 6-continued

Influence of dietary RAC and/or caffeine addition on carcass yield
from a subset of carcasses (n = 12 per treatment)

|  | Sex | | SED | Feeding Strategy | | SED | Significance | | |
|---|---|---|---|---|---|---|---|---|---|
|  | Female | Improvac | Sex | Control | RAC 7.5 ppm | RAC + caffeine | Diet | Sex | Diet | Sex × diet |
| Loin depth^^ (mm) | 58.6 | 58.3 | 0.54 | 57.8 | 58.2 | 59.3 | 0.63-0.65 | 0.56 | 0.078 | 0.71 |
| Cold carcass weight (kg) | 81.9 | 82.4 | 1.10 | 81.5 | 82.6 | 82.3 | 1.35-1.37 | 0.65 | 0.72 | 0.72 |
| Percentage Yield | | | | | | | | | | |
| Belly | 20.6 | 20.5 | 0.59 | 20.2 | 20.7 | 20.7 | 0.72-0.74 | 0.79 | 0.70 | 0.22 |
| Tenderloin | 3.66 | 3.66 | 0.142 | 3.52 | 3.65 | 3.82 | 0.173-0.176 | 0.99 | 0.23 | 0.78 |
| Middle total fat | 6.94 | 6.99 | 0.73 | 7.37 | 7.36 | 6.15 | 0.89-0.90 | 0.97 | 0.29 | 0.24 |
| Middle rind plus fat | 10.81 | 11.04 | 0.77 | 11.69 | 10.58 | 10.52 | 0.94-0.96 | 0.76 | 0.43 | 0.23 |
| Middle 60-65% chemical lean | 2.21 | 2.42 | 0.235 | 2.37 | 2.43 | 2.15 | 0.286-0.291 | 0.32 | 0.60 | 0.14 |
| Middle 80-85% chemical lean | 9.74 | 9.62 | 0.338 | 9.85 | 9.72 | 9.47 | 0.414-0.419 | 0.74 | 0.62 | 0.50 |
| Belly Ribs | 11.42 | 11.76 | 0.284 | 11.54 | 11.39 | 11.84 | 0.347-0.352 | 0.25 | 0.43 | 0.89 |
| Retail leg | 35.98 | 34.97 | 0.414 | 35.41 | 35.80 | 35.21 | 0.506-0.514 | 0.020 | 0.51 | 0.70 |
| Topside cap off rind less | 8.01 | 7.79 | 0.247 | 7.74 | 7.79 | 8.18 | 0.302-0.307 | 0.40 | 0.33 | 0.17 |
| Leg 90% chemical lean | 7.05 | 6.79 | 0.304 | 6.60 | 6.90 | 7.25 | 0.372-0.377 | 0.40 | 0.25 | 0.92 |

Implications

The results from this investigation indicated that under the conditions of two pigs per pen from 22-26 weeks of age, feed efficiency can be improved by almost 3% when pigs are offered the RAC+caffeine diet compared to RAC alone. The modest improvement in feed efficiency agrees with previous data and was supported by biologically significant reductions in P2 back fat depth. Although the number of carcasses followed through the boning room was small and insufficient to obtain enough statistical power, there were positive numerical trends in yield of commercially important cuts such as the tenderloin and belly ribs. The reduction in total fat from the middle was also a positive outcome.

Study 3—Influence of RAC+Caffeine Feeding Strategy Over Summer

It is known that the response of finisher pigs to dietary RAC is not constant over the duration of a finisher feeding regime but is most pronounced during the first 2 weeks of feeding and declines thereafter due to the down regulation of β-receptors. Several methods have been investigated by other groups in an effort to maintain the performance benefits of RAC over a longer feeding period. These methods have included using step up programs (cost/benefit can be marginal due to the higher RAC costs, silo management also difficult in large commercial operations) and the use of intermittent feeding (Australian Pork CRC project 2H-102).

Studies by the present Inventors investigating the growth performance, feed efficiency and carcass response to feeding RAC in combination with caffeine have indicated that caffeine may extend the response to RAC beyond the traditional 2-3 week feeding period. Caffeine can be included in finisher diets during autumn to cap finisher feed intake to more appropriate levels to limit excessive fat deposition. There may also be added benefits from including caffeine year round to improve the feed efficiency and P2 back fat response to RAC inclusion during the finisher period. There have recently been questions regarding the impact of this strategy on weight during the summer months when feed intakes are reduced naturally by the warmer temperatures. As such, the aim of this investigation is to determine the impact of the RAC+caffeine strategy on growth performance, feed efficiency and carcass characteristics when fed during summer conditions in southern Australia.

Materials and Methods

Animals and Treatments

A total of 701 pigs (female and immunocastrated males, Large White×Landrace, PrimeGro™ Genetics) were identified at 17 weeks of age in pens of 11-14 pigs of the same sex. All animals were selected to start the trial on the one day. Prior to the start of the trial, all pigs were offered a commercial grower diet (no Paylean) and had been in their allocated pens from 10 weeks of age. No remixing of pigs occurred before the start of the test period. At 17 weeks of age, pen weights were recorded (average pig weight 63.5 kg±0.38 kg) and pens randomly allocated within sex to one of 3 dietary treatments (A: Control, no RAC or caffeine, B: RAC 7.5 ppm, C: RAC+caffeine (RAC 7.5 ppm plus caffeine 0.5 kg/t). All diets were fed for the entire 35 day test period. The dietary compositions of the three experimental diets are displayed in Table 7. All diets were formulated to contain 0.56 g available lysine/MJ DE and 13.9 MJ DE/kg. Diets were pelleted and fed ad libitum from 17 weeks of age through to slaughter at 22 weeks of age. All animals had ad libitum access to water via nipple drinkers for the entire experimental period. Oxytetracycline was included in water for two days every fortnight for lawsonia control.

Management and Measures

Growth Performance

The priming Improvac™ vaccination was administered to the male pigs at 13 weeks of age and the second vaccination at 17 weeks of age (day 0 of the experimental period). Pen weights were recorded at the beginning of the experimental period (day 0, 17 weeks of age) and again at day 14 and day 35 (prior to slaughter). Pen feed Intakes were also recorded over these time periods as measured by feed disappearance and feed conversion efficiency subsequently calculated. All deaths and removals were recorded and taken into account when calculating feed intake and feed efficiency by the adjustment of the number of days that pigs were on trial.

Statistical Analyses

Data were subjected to an analysis of variance (ANOVA) with the main effects being dietary treatment and sex. Replicate (start date within week) was included in the analyses to account for the blocking factor. The experimental unit for all analyses was the pen of pigs. All analyses were performed using Genstat 8th Edition (Payne et al. 2005).

TABLE 7

Ingredient composition and analysed nutrient profile of each of the experimental finisher diets, % of diet (as fed basis).

|  | Control | RAC | RAC + Caffeine |
|---|---|---|---|
| Wheat | 82.1 | 82.1 | 82.1 |
| Millmix | 3.33 | 3.33 | 3.33 |
| Canola Meal 35% | 5.0 | 5.0 | 5.0 |
| Meat meal | 5.3 | 5.3 | 5.3 |
| Water | 1.0 | 1.0 | 1.0 |
| Natuphos 5000 | 0.01 | 0.01 | 0.01 |
| Tallow-Mixer | 1.17 | 1.17 | 1.17 |
| Limestone | 1.07 | 1.07 | 1.07 |
| DL-Methionine | 0.04 | 0.04 | 0.04 |
| Copper Proteinate | 0.10 | 0.10 | 0.10 |
| Paylean ™ Premix |  | 0.0375 | 0.0375 |
| Caffeine |  |  | 0.05 |
| Lysine Micro | 0.42 | 0.42 | 0.42 |
| Threonine Micro | 0.16 | 0.16 | 0.16 |
| Fysal SP Dry | 0.20 | 0.20 | 0.20 |
| Vitamin and Minerals | 0.096 | 0.096 | 0.096 |
| Salt Bin Micro | 0.20 | 0.20 | 0.20 |
| Salinodox 120 Micro | 0.05 | 0.05 | 0.05 |
| Estimated nutrient composition, %* | | | |
| DE, MJ/kg | 13.95 | 13.95 | 13.95 |
| Crude protein | 15.18 | 15.18 | 15.18 |
| Crude fat | 2.93 | 2.93 | 2.93 |
| Crude fibre | 3.09 | 3.09 | 3.09 |
| Available lysine:DE ratio g/MJ DE | 0.56 | 0.56 | 0.56 |

*Estimated from Rivalea Australia Pty Ltd composition data

Results

There were no, negative effects of the RAC+caffeine treatment on animal welfare during the study with the percentage of combined deaths and removals lower than the standard RAC treatment group (Table 8).

TABLE 8

Influence of dietary treatment on deaths and removals during the test period

|  | Deaths | | Removals | | |
|---|---|---|---|---|---|
|  | APP | Lame | APP | Unthrifty | Lame |
| Control |  |  | 1 |  | 1/234 (0.4%) |
| RAC | 2 | 2 |  | 1 | 5/228 (2.2%) |
| RAC + caffeine | 3 |  |  |  | 1 | 4/239 (1.6%) |

The impact of the RAC+caffeine strategy over summer on growth performance and carcase composition is displayed in Table 8. Both sexes responded similarly to the dietary treatments, with no diet by sex interactions observed. During the initial 14 day period, feed intake and growth rate were similar between the control pigs and those offered the RAC diet, while pigs offered the RAC+caffeine diet consumed less feed and grew approximately 9% slower compared to the controls. Feed efficiency was not significantly influenced by dietary treatment during this time, although both the RAC and RAC+caffeine treatments were approximately 4% more efficient than the control animals. Feed intake remained lower in the RAC+caffeine treatment group from 14 to 35 days, although daily gain was maintained at a similar rate to the other groups. The flow on effect of this was a 5.4% improvement in feed efficiency in the RAC+caffeine treatment group compared to those offered the RAC alone during this late finisher period. Over the entire test period, there was no benefit from the addition of 7.5 ppm RAC alone, with these pigs displaying similar growth rates and feed efficiency to the control animals. In comparison, pigs offered the RAC+caffeine diet consumed 7.6% less feed and grew 5% slower than the RAC pigs. These differences in intake and rate of gain resulted in a slight improvement in feed efficiency over the entire test period (FCR 2.48 RAC and 2.43 in the RAC+caffeine treatment group, P=0.20).

The impacts of the dietary treatments on carcase characteristics are also displayed in Table 9. Carcase weights have not been reported due to a mechanical breakdown at the abattoir after the pigs had arrived in lairage, which required pigs to be fed a maintenance ration for several days at the abattoir before slaughter. Final live weight is however reported (day 35) and shows a slight reduction in carcase weight with the RAC+caffeine diet, although not significant. Without being able to take carcass weight into consideration, P2 was reduced by 1.3 mm compared to the RAC treatment group, while loin death was increased by 0.8 mm.

TABLE 9

Impact of the P&C strategy over summer on growth performance and carcase characteristics

|  | Sex | | Dietary treatment | | | SED | | Significance | |
|---|---|---|---|---|---|---|---|---|---|
|  | | | | | | | | | Sex × |
|  | Female | Improvac | Control | RAC | RAC + Caff | Diet | Sex | Diet | Diet |
| Live weight (kg) | | | | | | | | | |
| Day 0 | 62.8 | 64.3 | 63.4 | 63.5 | 63.6 | 0.93 | 0.044 | 0.98 | 0.99 |
| Day 14 | 77.3 | 80.0 | 78.9 | 79.4 | 77.7 | 1.09 | 0.005 | 0.28 | 0.65 |
| Day 35 | 95.8 | 104.1 | 100.9 | 100.5 | 98.6 | 1.36 | <0.001 | 0.21 | 0.95 |
| Average daily gain (kg/d) | | | | | | | | | |

TABLE 9-continued

Impact of the P&C strategy over summer on growth performance and carcase characteristics

| | Sex | | Dietary treatment | | | SED | Significance | | Sex × |
|---|---|---|---|---|---|---|---|---|---|
| | Female | Improvac | Control | RAC | RAC + Caff | Diet | Sex | Diet | Diet |
| Day 0-14 | 1.041 | 1.117 | 1.102 | 1.132 | 1.002 | 0.055 | 0.094 | 0.054 | 0.40 |
| Day 14-35 | 0.881 | 1.151 | 1.047 | 1.004 | 0.996 | 0.043 | <0.001 | 0.44 | 0.28 |
| Day 0-35 | 0.945 | 1.137 | 1.069 | 1.056 | 0.998 | 0.022 | <0.001 | 0.007 | 0.86 |
| Average daily feed intake (kg/d) | | | | | | | | | |
| Day 0-14 | 2.24 | 2.34 | 2.38 | 2.36 | 2.13 | 0.052 | 0.018 | <0.001 | 0.24 |
| Day 14-35 | 2.41 | 3.08 | 2.83 | 2.79 | 2.61 | 0.057 | <0.001 | <0.001 | 0.75 |
| Day 0-35 | 2.34 | 2.78 | 2.65 | 2.62 | 2.42 | 0.043 | <0.001 | <0.001 | 0.41 |
| Feed conversion ratio (kg/kg) | | | | | | | | | |
| Day 0-14 | 2.17 | 2.17 | 2.23 | 2.15 | 2.14 | 0.133 | 0.99 | 0.76 | 0.64 |
| Day 14-35 | 2.77 | 2.71 | 2.77 | 2.80 | 2.65 | 0.104 | 0.47 | 0.32 | 0.096 |
| Day 0-35 | 2.48 | 2.45 | 2.48 | 2.48 | 2.43 | 0.034 | 0.36 | 0.20 | 0.074 |
| Carcase Characteristics* | | | | | | | | | |
| P2 (mm) | 10.6 | 11.3 | 11.5 | 11.3 | 10.0 | 0.22 | <0.001 | <0.001 | 0.61 |
| Loin muscle depth (mm) | 58.8 | 58.4 | 58.2 | 58.4 | 59.2 | 0.14 | 0.004 | <0.001 | 0.99 |

*Carcase weight and dressing percentage not reported due to a breakdown at the abattoir.

Discussion

The limited response to dietary RAC at 7.5 ppm again highlights the issue in utilising this feed additive over the summer period. The primary response to RAC was observed in the initial 14 day period with a moderate improvement (approximately 4%) in feed efficiency compared to the control treatment. The summer of the test was very warm, with only 7 days during the period of this investigation in which the maximum daily temperature was below 30° C. and only 15 days in which the minimum temperature was below 15° C.). Average daily feed intakes were however reasonable despite the high temperatures during the test period (average 2.62 kg/d). Pervious investigations have suggested that the response to RAC is limited during the summer period due to the lower feed intakes commonly observed and therefore the reduced intake of lysine/pig/day. In this study, pigs offered the RAC diet consumed on average 2.6 kg feed/day, resulting in an average intake of available lysine per pig of 20.4 g/day. Feed intake was however lower during the initial 14 days of the test period, resulting in marginally lower intakes of available lysine (average feed intake 2.36 kg/day and 18.4 g available lysine/day). It is hypothesised that this reduction in total intake of available lysine per day limited the response to RAC during the time when the response is normally most pronounced.

The use of the combination strategy (RAC+caffeine) was once again very promising. The strategy resulted in a 7.6% reduction in feed intake over the entire test period when compared to the pigs offered RAC alone. While the improvement in feed efficiency was not statistically significant in this study, this response has been fairly consistent in other studies with the improvement most prominent during the later feeding period when the response to RAC generally declines. The 2 kg reduction in final live weight was offset by a substantial reduction in P2 back fat depth (almost 10%)—this is particularly important as producers move to heavier carcase weights and try to limit any negative impacts on carcass P2.

Implications

The response to RAC at 7.5 ppm over the summer period was once again negligible, with no overall improvement in feed efficiency, daily gain or carcass composition. However, when caffeine was included in the RAC diet, substantial improvements were made in carcass P2 and loin depth, with more moderate effects on feed efficiency and final live weight. The push for heavier carcass weights while still maintaining a reasonable P2 back fat depth brings means the present invention is particularly relevant. The use of 7.5 ppm RAC in combination with 0.5 kg/t caffeine is useful in situations where P2 back fat depth should be controlled over summer.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An animal feed supplement comprising a synergistic combination of ractopamine and caffeine for increasing response in an animal to ractopamine in an animal feed.

2. The animal feed supplement according to claim 1 wherein the ractopamine is ractopamine hydrochloride.

3. The animal feed supplement according to claim 1 or 2 having a ratio of ractopamine to caffeine of from 1:100 to 1:10.

4. The animal feed supplement according to claim 3 wherein the ratio of ractopamine to caffeine is 1:70.

5. The animal feed supplement according to claim 1 containing from 1 to 50 g/kg ractopamine and from 50 to 1000 g/kg caffeine for mixing with bulk complete animal feed to provide a desired final concentration of ractopamine and caffeine to the animal feed.

6. The animal feed supplement according to claim 5 containing at least 10 g/kg ractopamine hydrochloride and at least 700 g/kg caffeine.

7. The animal feed supplement according to claim 1 containing at least about 1% (w/w) ractopamine and at least about 50% (w/w) caffeine.

8. A method of increasing response to ractopamine of a pig, the method comprising feeding to a pig over a period of time an animal feed containing animal feed supplement according to claim 1.

9. The method according to claim 8 wherein the ractopamine response is improving feed efficiency of the pig.

10. A method of increasing ractopamine response in a pig, the method comprising feeding a pig an animal feed containing a synergistic combination of ractopamine and caffeine to extend the response to ractopamine in the pig.

11. The method according to claim 10 wherein the ractopamine response is improved feed efficiency in the pig.

12. The method according to claim 10 wherein the ractopamine response is extended in the pig past 3 weeks.

13. The method according to claim 12 wherein the pig is fed the animal feed over a period of at least 28 days.

14. The method according to claim 10 wherein the response to ractopamine in the pig is extended for at least 14 days.

15. The method according to claim 10 wherein the pig is fed the animal feed over a period of up to 60 days.

16. The method according to claim 15 where the pig is fed the animal feed for a period of 21 to 35 days.

17. The method according to claim 10 wherein the animal feed contains from 1 mg/kg to 50 mg/kg (w/w) ractopamine and from 0.02 g/kg to 5 g/kg (w/w) caffeine.

18. The method according to claim 17 wherein the animal feed contains from 5 mg/kg to 20 mg/kg (w/w) ractopamine and from 0.1 g/kg to 1 g/kg (w/w) caffeine.

19. The method according to claim 18 wherein the animal feed contains 7.5 mg/kg ractopamine and 0.5 g/kg caffeine.

20. The method according to claim 10 wherein the animal feed is a typical pig finishing feed containing essential dietary requirements for a pig.

21. The method according to claim 20 wherein the animal feed contains a range of energy and protein sources selected from wheat, barley, sorghum, corn, soybean meal, lupins, canola meal, meat meal and bone meal.

22. The method according to claim 11 wherein the feed efficiency of a pig is improved by 1 to 5%.

23. The method according to claim 11 wherein the feed efficiency of a pig is up to 5% improvement above feeding ractopamine alone over the same period.

* * * * *